United States Patent [19]

Sano et al.

[11] Patent Number: 5,300,634
[45] Date of Patent: Apr. 5, 1994

[54] PROCESS FOR PRODUCING MALTOOLIGOSACCHARIDE DERIVATIVE

[75] Inventors: Atsunori Sano, Kawagoe; Naoki Teno, Amagasaki, both of Japan

[73] Assignee: Wako Pure Chemical Industries, Ltd., Osaka, Japan

[21] Appl. No.: 878,266

[22] Filed: May 4, 1992

[30] Foreign Application Priority Data

May 7, 1991 [JP] Japan .................. 3-131880

[51] Int. Cl.$^5$ ........................................ C07H 15/00
[52] U.S. Cl. ...................... 536/17.1; 435/18; 435/22; 536/4.1; 536/17.3; 536/17.9
[58] Field of Search .................. 435/18, 22; 536/17.1, 536/4.1, 17.9, 17.3

[56] References Cited

U.S. PATENT DOCUMENTS

| | | | |
|---|---|---|---|
| 4,544,631 | 10/1985 | Rauscher et al. | 435/22 |
| 4,681,841 | 7/1987 | Matsumoto et al. | 435/22 |
| 4,709,020 | 11/1987 | Rauscher et al. | 536/17.8 |
| 4,762,917 | 8/1988 | Ikenaka et al. | 536/4.1 |
| 4,818,692 | 4/1989 | Rauscher et al. | 435/18 |
| 4,843,154 | 6/1989 | Klein et al. | 536/17.9 |
| 4,963,479 | 10/1990 | Chavez et al. | 435/22 |
| 4,987,067 | 1/1991 | Ishimara et al. | 536/18.1 |
| 5,011,923 | 4/1991 | Ono et al. | 536/17.9 |
| 5,068,183 | 11/1991 | Ogawa et al. | 435/22 |
| 5,108,913 | 4/1992 | Rauscher et al. | 435/101 |
| 5,158,872 | 10/1992 | Chavez et al. | 435/22 |
| 5,192,666 | 3/1993 | Ikenaka et al. | 536/17.1 |

FOREIGN PATENT DOCUMENTS 0135758 4/1985 European Pat. Off. .
0171960 2/1986 European Pat. Off. .

OTHER PUBLICATIONS

Liotta, L. J. et al. "Selective Benzylation of Alcohols and Amines Under Mild Conditions." *Pergamon Press plc*, vol. 30, No. 36, pp. 4759–4762.
Kato, J. et al. "A Novel Method for the Preparation of Symetrical and Unsymmetrical Ethers. Trityl Perchlorate Promoted Reduction of Carbonyl Compounds with Triethylsilane." *The Chemical Society of Japan*, pp. 743–746.
Chemistry Letters, No. 1, 1985, Japan, J. Kato et al.

*Primary Examiner*—Herbert J. Lilling
*Attorney, Agent, or Firm*—Armstrong, Westerman, Hattori, McLeland & Naughton

[57] ABSTRACT

A maltooligosaccharide derivative very useful, for example, as a precursor of a modified oligosaccharide derivative having one or more modifying groups at the 6-position or the 4- and 6-positions of the non-reducing end glucose residue which can be effectively used as a substrate for determining α-amylase activity or an intermediate thereof, can be produced by reacting a compound of the formula:

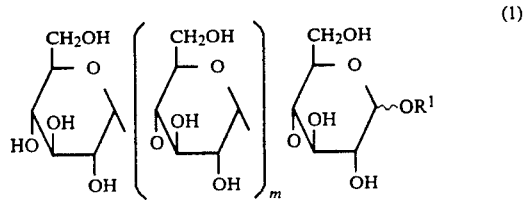

(1)

with a compound of the formula:

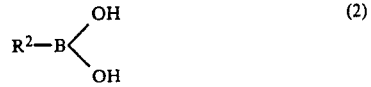

(2)

to convert at least the hydroxyl groups at the 4- and 6-positions of non-reducing end glucose residue of the compound of the formula (1) into a cyclic boric acid ester, acylating the reaction product, and then treating the acylated product.

2 Claims, No Drawings

PROCESS FOR PRODUCING MALTOOLIGOSACCHARIDE DERIVATIVE

BACKGROUND OF THE INVENTION

This invention relates to a process for producing a maltooligosaccharide derivative very useful, for example, as a precursor of a modified oligosaccharide derivative having one or more modifying groups at the 6-position or the 4- and 6-positions of the non-reducing-end glucose residue, and having or not having an optically measurable group at the reducing end, said modified oligosaccharide derivative being effectively usable as a substrate for determining α-amylase activity, or an intermediate of the substrate; and a process for producing the substrate for determining α-amylase activity, by use of said maltooligosaccharide derivative.

Determination of α-amylase activity in samples, in particular, saliva, sancreatic juice, blood and urine in a human body gives an important indication for medical diagnoses. For example, in the case of pancreatisis, pancreas cancer and parotiditis, the level of α-amylase activity in blood and urine is much higher than its usual level. For the determination, there has come to be generally employed in recent years a coupling enzyme method using as substrate a maltooligosaccharide having a color-producing group at the reducing end and a non-reducing end glucose residue modified at the 6-position or the 4- and 6-positions.

In the synthesis of such a substrate having a non-reducing end glucose residue modified only at the 6-position or the 4- and 6-positions, if there is a common intermediate which permits free and easy introduction of various modifying groups only into the 6-position or the 4- and 6-positions of the non-reducing end glucose residue, it becomes possible to synthesize rapidly and efficiently a substrate for determining α-amylase activity or an intermediate thereof, which has higher performance characteristics and a newer function. Therefore, the production and development of a substrate for determining α-amylase activity proceed rapidly, and hence the common intermediate is of high utility value.

Japanese Patent Unexamined Publication Nos. 60-54395 (U.S. Pat. Nos. 4,709,020 and 4,818,692) and 2-49796 (U.S. Pat. No. 5,011,923) disclose a polyacetylmaltooligosaccharide derivative retaining the hydroxyl groups at the 4- and 6-positions of the non-reducing end glucose residue, and a process for producing the same. Utilization of these intermediates permits selective and easy synthesis of a substrate having a non-reducing end glucose residue modified only in the hydroxyl group at the 6-position and a substrate having a non-reducing end glucose residue modified at the 4- and 6-positions with bridge type blocking groups.

However, the synthetic process of the polyacetylmaltooligosaccharide derivative retaining the hydroxyl groups at the 4- and 6-positions of the non-reducing end glucose residue which has been disclosed in the above-mentioned Japanese Patent Unexamined Publication Nos. 60-54395 and 2-49796, has the following defect. The synthetic process uses a commercially available oligosaccharide derivative as a starting material and comprises three independent steps, i.e., a step of blocking the 4- and 6-positions, an acylation step and a deblocking step. Moreover, as a blocking group for the 4- and 6-positions, there is used a cyclic ketal (or acetal) type blocking group such as ethylidene group, isopropylidene group, benzylidene group or the like. Therefore, both the blocking step and the deblocking step require severe conditions and a troublesome procedure, so that the kind of the color-producing group at the reducing end is unavoidably limited.

Accordingly, there has been an eager desire for the advent of a process for producing a polyacrylmaltooligosaccharide derivative retaining the hydroxyl groups at the 4- and 6-positions of the non-reducing end glucose residue, easily in high yield under mild conditions by using a commercially available oligosaccharide derivative as a starting material.

SUMMARY OF THE INVENTION

This invention was made in view of such conditions and is intended to provide a very effective production process of a maltooligosaccharide derivative which permits free introduction of various modifying groups into the 6-position or the 4- and 6-positions of the non-reducing end glucose residue, and a process for producing a substrate for determining α-amylase activity or an intermediate thereof, which has one or more modifying groups at the 6-position or the 4- and 6-positions of the non-reducing end glucose residue and one or no optically measurable group at the reducing end, via said maltooligosaccharide derivative.

This invention provides a process for producing a maltooligosaccharide derivative comprising glucose units in a number of n represented by the formula:

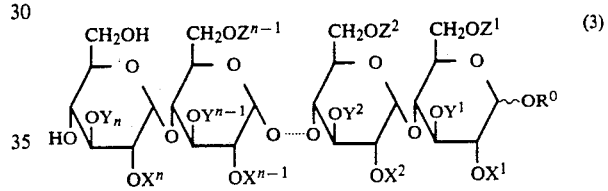

wherein $R^0$ is an optically measurable group or an acyl group; $X^1$ through $X^n$, $Y^1$ through $Y^n$ and $Z^1$ through $Z^{n-1}$ are independently an acyl group or a hydrogen atom provided that $X^1$ through $X^n$, $Y^1$ through $Y^n$ and $Z^1$ through $Z^{n-1}$ cannot be hydrogen atoms at the same time; n is an integer of 3 to 7, which comprises reacting a compound represented by the formula:

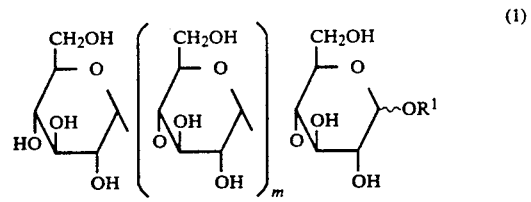

wherein $R^1$ is an optically measurable group or a hydrogen atom; and m is an integer of 1 to 5, with a compound represented by the formula:

wherein $R^2$ is an alkyl group, a hydroxyl group, an alkenyl group, an aralkyl group or an aryl group which may have one or more substituents selected from lower alkyl groups, lower alkoxy groups, nitro groups, amino groups and halogen atoms, said aryl group which may have one or more substituents being able to be a part of the constituent of a polymer, to convert at least the hydroxyl groups at the 4-position and the 6-position of the non-reducing end glucose residue of the compound of the formula (1) into a cyclic boric acid ester, acylating the reaction product, and then treating the acylated product with water.

This invention further provides a process for producing a compound represented by the formula:

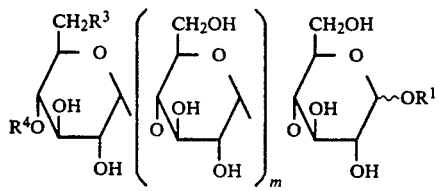
(4)

wherein $R^3$ is an aralkyloxy group which may have one or more substituents (said substituents being lower alkyl groups, lower alkoxy groups, amino groups, lower-alkyl-substituted amino groups, carboxyl groups, lower alkoxycarbonyl groups, hydroxyl groups, sulfonic acid groups, nitro groups or halogen atoms), a lower alkoxy group, a lower alkenyloxy group, an aryloxy group which may have one or more substituents (said substituents being the same as those for the above-mentioned aralkyloxy group), a pyridylmethyloxy group which may have one or more substituents (said substituents being the same as those for the above-mentioned aralkyloxy group), an amino group which may have one or more substituents (said substituents being lower alkyl groups, lower hydroxyalkyl groups, aralkyl groups, lower-alkyl-substituted aralkyl groups, lower-alkoxy-substituted aralkyl groups, aryl groups, lower-alkoxy-substituted aryl groups, pyridyl groups, lower-alkyl-substituted pyridyl groups or lower-alkoxy-substituted pyridyl groups), a trialkylsilyloxy group, or an alkyldiphenylsilyloxy group; $R^4$ is a hydrogen atom, $R^3$ and $R^4$ being able to be taken together to represent a methylene ketal which may have one or more substituents (said substituents being lower alkyl groups, lower alkoxy groups, aralkyl groups, or aryl groups which may have one or more substituents); and $R^1$ and m are as defined above, which comprises replacing the hydroxyl group at the 6-position or each of the 4- and 6-positions of the non-reducing end glucose residue of a maltooligosaccharide derivative comprising glucose units in a number of n represented by the formula:

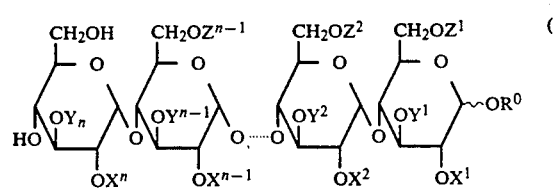
(3)

wherein $R^0$, $X^1$ through $X^n$, $Y^1$ through $Y^n$, $Z^1$ through $Z^{n-1}$ and n are as defined above, by a modifying group other than acyl groups, and then subjecting the maltooligosaccharide derivative thus treated to deacylation, said maltooligosaccharide derivative being obtained by reacting a compound represented by the formula:

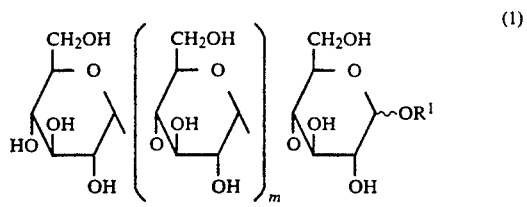
(1)

wherein $R^1$ and m are as defined above, with a compound represented by the formula:

(2)

wherein $R^2$ is as defined above, to convert at least the hydroxyl groups at the 4-position and the 6-position of the non-reducing end glucose residue of the compound of the formula (1) into a cyclic boric acid ester, acylating the reaction product, and then treating the acylated product with water.

DESCRIPTION OF THE PREFERRED EMBODIMENTS

The present inventors earnestly investigated in order to achieve the above objects, and consequently found the following. In the production of a polyacrylmaltooligosaccharide derivative of the formula (3) which has one or no color-producing group at the reducing end and retains hydroxyl groups at the 4- and 6-positions of the non-reducing end glucose residue, when the hydroxyl groups at the 4- and 6-positions of the non-reducing end glucose residue are blocked by converting them into a cyclic boric acid ester by use of a boric acid compound of the formula (2), the blocking group is much easier to remove than 4- and 6-positions bridge type blocking groups such as benzylidene group, ethylidene group, isopropylidene group, etc. which have been conventionally used. Moreover, it exists very stably without being removed under acylation conditions. Thus, the present inventors have established the process of this invention which makes it possible to produce said polyacylmaltooligosaccharide derivative very easily in high yield.

In the formulas (1), (3) and (4), as the optically measurable group represented by $R^1$ or $R^0$, any group may be used so long as it is releasable from a glucoside form by the action (e.g. hydrolysis) of an enzyme such as glucoamylase[E.C.3.2.1.3.], α-glucosidase[E.C.3.2.1.20.], β-glucosidase[E.C.3.2.1.21.], isomaltase[E.C.3.2.1.10.] or β-amylase[E.C.3.2.1.2.], and in addition after being released, it has any one of the following properties: it can absorb a visible light or an ultraviolet light in itself, like nitrophenol or derivatives thereof; it can emit fluorescence in itself, like substituted or unsubstituted umbelliferone and derivatives thereof; it is coupled to a coupler by the action of an oxidase such as catechol oxidase, laccase, tyrosinase or monophenol oxidase to form a dye; it is coupled to a coupler by an oxidizing agent to form a dye. Although such optically measurable groups are known to those skilled in the art and need not be particularly explained in detail, typical examples of the optically measurable group are unsubstituted aryl groups such as phenyl, 1-naphthyl, 2-methylphenyl, 2-methyl-1-naphtyl, etc.;

substituted aryl groups such as 4-nitrophenyl, 3-nitrophenyl, 2-chlorophenyl, 4-chlorophenyl, 2,6-dichlorophenyl, 2-chloro-4-nitrophenyl, 2,6-dichloro-4-nitrophenyl, 2-methoxyphenyl, 4-methoxyphenyl, 2-carboxyphenyl, 2-sulfophenyl, 2-sulfo-1-naphtyl, 2-carboxy-1-naphtyl, etc.; unsubstituted umbelliferyl group; substituted umbelliferyl groups such as 4-methylumbelliferyl, 4-trifluoromethylumbelliferyl, etc.; unsubstituted indoxyl group; and substituted indoxyl groups such as 5-bromoindoxyl, 4-chloro-3-bromoindoxyl, etc.

$R^0$ in the formula (3) includes acyl groups in addition to these optionally measurable groups. $R^1$ in the formulas (1) and (4) includes a hydrogen atom in addition to the optionally measurable groups.

As the acyl groups represented by $X^1, X^2, \ldots X^{n-1}, X^n, Y^1, Y^2, \ldots Y^{n-1}, Y^n, Z^1, Z^2, \ldots Z^{n-2}, Z^{n-1}$ and $R^0$ in the formula (4), there can be exemplified aliphatic acyl groups such as acetyl, monochloroacetyl, trichloroacetyl, trifluoroacetyl, propionyl, butyryl, levulinoyl, etc.; and aromatic acyl groups such as benzoyl, p-methoxybenzoyl, etc. Usually, there can be preferably exemplified acetyl group and benzoyl group which are obtained from inexpensive and easily available reagents.

In the formulas (1) and (4), m is an integer of 1 to 5, and in the formula (3), n is an integer of 3 to 7. That is, the compounds of the formulas (1), (3) and (4) are derivatives of maltotriose, maltotetraose, maltopentaose, maltohexaose or maltoheptaose.

In the formula (2), for $R^2$, the alkyl group includes, for example, alkyl groups preferably having 1 to 6 carbon atoms (e.g. methyl group, ethyl group, propyl group, butyl group, amyl group and hexyl group) which may be linear, branched or cyclic. The alkenyl group includes, for example, alkenyl groups preferably having 2 to 6 carbon atoms, such as ethenyl, 2-propenyl, 2-butenyl, etc. The aralkyl group includes, for example, benzyl group, phenethyl group, and phenylpropyl group. The aryl group which may have one or more substituents includes, for example, phenyl group, tolyl group, ethylphenyl group, methoxyphenyl group, ethoxyphenyl group, aminophenyl group, nitrophenyl group, chlorophenyl group, bromophenyl group, naphthyl group, methylnaphthyl group, and methoxynaphthyl group. These aryl groups which may have one or more substituents may be a part of the constituent of a polymer. Specific examples of the polymer are styrene-divinylbenzene copolymers, etc. As $R^2$ in the formula (2), hydroxyl group can be exemplified in addition to the groups exemplified above.

In the formula (4), as the substituents on the three groups represented by $R^3$, i.e., the aralkyloxy group which may have one or more substituents, the aryloxy group which may have one or more substituents and the pyridylmethyloxy group which may have one or more substituents, there can be exemplified lower alkyl groups (i.e. methyl group, ethyl group, propyl group, butyl group, etc.) which may be either linear or branched, lower alkoxy groups (e.g. methoxy group, ethoxy group, propoxy group, butoxy group, etc.) which may be either linear or branched, substituted amino groups (e.g. dimethylamino group, diethylamino group, N-ethyl-N-(β-hydroxyethyl)amino group, etc.), carboxyl group, lower alkoxycarbonyl groups (e.g. methoxycarbonyl group, ethoxycarbonyl group, etc.), sulfonic acid group, hydroxyl group, nitro group, and halogen atoms (e.g. chlorine, bromine, iodine, etc.). The aralkyloxy group includes, for example, benzyloxy group, phenethyloxy group, phenylpropyloxy group, trityloxy group, and diphenylmethyloxy group. The aryloxy group includes, for example, phenoxy group and naphthyloxy group. The lower alkoxy group includes, for example, linear, branched or cyclic alkoxy groups preferably having 1 to 6 carbon atoms, such as methoxy, ethoxy, n-propoxy isopropoxy, n-butoxy, tert-butoxy, n-pentyloxy, isoamyloxy, n-hexyloxy, cyclopentyloxy, cyclohexyoxy, etc. The lower alkenyloxy group includes alkenyloxy groups preferably having 2 to 6 carbon atoms, such as ethenyloxy, 2-propenyloxy, 2-butenyloxy, etc. The substituents on the amino group which may have one or more substituents include, for example, lower alkyl groups (e.g. methyl group, ethyl group, propyl group, butyl group, amyl group, etc.) which may be either linear or branched, lower hydroxyalkyl groups (e.g. hydroxyethyl group, hydroxypropyl group, hydroxybutyl group, etc.), substituted or unsubstituted aralkyl groups (e.g. benzyl group, phenethyl group, methylbenzyl group, methylphenethyl group, methoxybenzyl group, methoxyphenethyl group, ethoxybenzyl group, ethoxyphenethyl group, etc.), substituted or unsubstituted aryl groups (e.g. phenyl group, alkyl-substituted phenyl groups such as tolyl group, ethylphenyl group, propylphenyl group, etc., alkoxy-substituted phenyl groups such as methoxyphenyl group, ethoxy phenyl group, propoxyphenyl group, etc., naphthyl group, alkyl-substituted or alkoxy-substituted naphthyl groups such as methylnaphthyl group, methoxynaphthyl group, etc.), and substituted or unsubstituted pyridyl groups (e.g. pyridyl group, alkyl-substituted or alkoxy-substituted pyridyl groups such as methylpyridyl group, ethylpyridyl group, methoxypyridyl group, ethoxypyridyl group, etc.). The trialkylsilyloxy group includes, for example, trimethylsilyloxy group and dimethyl-tert-butylsilyloxy group. The alkyldiphenylsilyloxy group includes, for example, diphenylmethylsilyloxy group and diphenyl-tert-butylsilyloxy group.

When $R^3$ and $R^4$ are taken together to represent a methylene ketal which may have one or more substituents, the substituents include, for example, linear, branched or cyclic alkyl groups preferably having 1 to 6 carbon atoms (e.g. methyl group, ethyl group, n-propyl, isopropyl group, n-butyl group, tert-butyl group, n-pentyl group, isoamyl group, n-hexyl group, cyclopentyl group, cyclohexyl group, etc.), lower alkoxy groups (e.g. methoxy group, ethoxy group, propoxy group, butoxy group, etc.) which may be either linear or branched, aralkyl groups (e.g. benzyl group, phenethyl group, phenylpropyl group, etc.), and substituted or unsubstituted aryl groups (e.g. phenyl group, tolyl group, ethylphenyl group, methoxyphenyl group, ethoxyphenyl group, aminophenyl group, nitrophenyl group, chlorophenyl group, bromophenyl group, naphthyl group, methylnaphthyl group, methoxynaphthyl group, etc.).

The present invention's process for producing a compound of the formula:

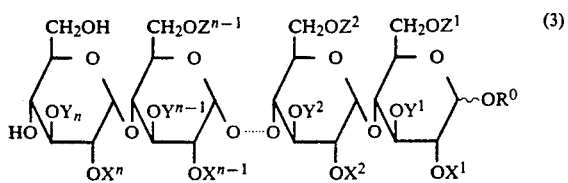

wherein $R^1, X^1, X^2, \ldots X^{n-1}, X^n, Y^1, Y^2, \ldots Y^{n-1}, Y^n, Z^1, Z^2, \ldots Z^{n-2}, Z^{n-1}$ and n are as defined above (hereinafter abbreviated as "compound (3)") is practiced substantially as follows.

First, a compound of the formula:

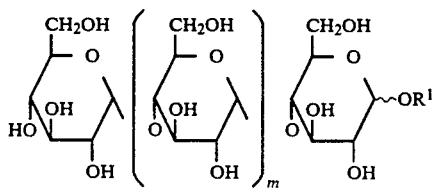

wherein $R^1$ and m are as defined above (hereinafter abbreviated as "compound (1)") is reacted with a compound of the formula:

wherein $R^2$ is as defined above (hereinafter abbreviated as "compound (2)") to obtain a reaction intermediate formed by conversion of at least the hydroxyl groups at the 4- and 6-positions of the non-reducing end glucose residue of the compound (1) into a cyclic boric acid ester. Specific examples of the compound (2) used here are relatively generally used compounds such as methylboric acid, ethylboric acid, butylboric acid, phenylboric acid, boric acid, phenylboric acid polymers, etc. Of these compounds, there are preferably used inexpensive and easily available compounds such as methylboric acid, butylboric acid, phenylboric acid, etc., and those which can be used repeatedly such as phenylboric acid polymers, etc. Although it is sufficient that the reaction of the compound (1) with the compound (2) is carried out merely by mixing them, the yield can be increased by eliminating by-produced water from the system by a procedure such as distilling-off under reduced pressure. In this case, employment of a dehydrating agent such as molecular reives is also effective. The compound (2) is used in an amount of about 1 to about 10 moles, preferably 1 to 5 moles, more preferably 2 to 3 moles, per mole of the compound (1). A solvent for reaction is not always necessary. When it is used, solvents capable of dissolving the compound (1), for example, N,N-dimethylformamide (DMF), dimethylacetamide (DMAC), dimethyl sulfoxide (DMSO), and pyridine are preferable. As to the reaction temperature, the reaction can be carried out in a wide temperature range of from ice-cooling to with heating, preferably room temperature to 100° C., more preferably 40° to 60° C. Although the reaction time, as a matter of course, varies depending on the reaction temperature, the solvent and other conditions, it is usually several tens minutes to several days. It is sufficient that the progress of the reaction is followed by an analytical means such as TLC, NMR or the like. Next, the product (the reaction intermediate) is acylated. In this case, although the product may be acylated after its isolation by a column chromatography, etc., it is preferable to subject the reaction solution to acylation as it is without isolating the product because this procedure is simpler and easier.

It is sufficient that the acylation reaction is carried out in the presence of a base such as pyridine, N,N-dimethylaminopyridine, or the like by a conventional method by using acetic anhydride, acetyl chloride, benzoyl chloride or the like as an acylating agent, in a larger amount, preferably 2 to 5 times as much as the theoretical amount. The acylation is usually carried out with ice-cooling or upto 100° C., preferably at room temperature to 40° C. After the acylation reaction, when the reaction solution is poured into water, the surplus acrylating agent is decomposed, and at the same time, the boric acid ester previously formed is decomposed, whereby the desired compound (3) is produced. After completion of this reaction, the desired compound is isolated by a conventional after-treatment, for example, as follows. When the end product is obtained as crystals, it is collected by filtration. When the end product is obtained as an oily substance, it is extracted with a solvent.

The compound (3) thus obtained is a mixture of several components different in the amount of acyl group introduced. Although the components may, if necessary, be separated and purified by column chromatography, recrystallization, etc., they are usually usable as they are (as a mixture thereof) without any trouble, for the hereinafter described production of, for example, a useful substrate for determining α-amylase which has a modifying group at the 6-position or the 4- and 6-positions of the non-reducing end glucose residue. Therefore, when used for such a purpose, the components need not be particularly separated and purified.

When a phenylboric acid polymer is used as the compound (2) in the reaction of the compound (1) with the compound (2), the unreacted compound (1) can be recovered without deterioration of its quality, and the phenylboric acid polymer can also be used repeatedly. Therefore, when the compound (3) is produced on an industrial scale, a great reduction of the production cost can be expected.

For blocking the hydroxyl groups at the 4- and 6-positions of non-reducing end glucose residue of the compound (1), blocking groups such as ethylidene group, propylidene group, benzylidene group, etc. have heretofore been generally used. At the time of the blocking, these blocking groups require a reaction under acidic conditions for a long period of time. Therefore, when a color-producing group easily dissociable under acidic conditions (e.g. 2,6-dichlorophenyl group or 2-chloro-4-nitrophenyl group) has been attached to the reducing end glucose residue of the compound (1), the color-producing group tends to be released. Moreover, the blocking groups require a reaction under acidic conditions for a long period of time also at the time of removing them and hence involve the same problem as that caused at the time of the blocking. Therefore, there has been a desire to seek improvement in them. In addition, they involve another problem in that the above reactions should be carried out stepwise, resulting in a large number of steps for the production.

On the other hand, the process of this invention requires no acidic conditions at the time of the blocking and at the time of the deblocking, resulting in permitting easy blocking and deblocking. Therefore, said process can be applied without any trouble also to the above-mentioned compound (1) having an easily releasable color-producing group, and makes it possible to synthesize the compound (3) by a one-pot reaction requiring no isolation of an intermediate, resulting in a simplified procedure.

As the compound (1) used as a starting material, a commercially available one may be used as it is. When the compound (1) is not on the market, it may be synthesized according to, for example, the method described in Carbohydr. Res., 61, 359–368 (1978), Japanese Patent Unexamined Publication No. 53-12831 (British Patent 1,570,152), etc.

From the maltooligosaccharide derivative of the formula (3) thus obtained, a substrate for determining α-amylase activity or an intermediate thereof which is represented by the formula:

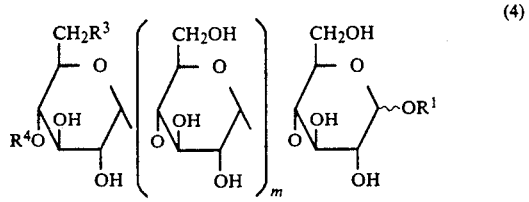

(4)

wherein $R^1$, $R^3$, $R^4$ and m are as defined above (hereinafter abbreviated as "compound (4)"), can easily be synthesized by replacing the hydroxyl group at the 6-position or the 4- and 6-positions of non-reducing end residue of the derivative by a modifying group other than acyl groups, and then subjecting the thus treated derivative to deacylation.

For example, in the case of an ether type maltooligosaccharide modified in such a way that in this compound (4), $R^4$ is a hydrogen atom and $R^3$ is an unsubstituted benzyloxy group, a substituted benzyloxy group, a pyridylmethyloxy group, an alkoxy group, an alkenyloxy group, an unsubstituted aryloxy group, a substituted aryloxy group or the like, the object can easily be achieved by introducing a corresponding modifying group selectively into the 6-position of non-reducing end glucose residue of the compound (3), and then subjecting the thus treated compound (3) to deacylation. An explanation is given below by giving specific examples. For example, a compound (4) wherein $R^3$ is a benzyloxy group and $R^4$ is a hydrogen atom, can easily be synthesized by reacting phenyldiazomethane as a benzylating agent with the compound (3) in the presence of an acid catalyst such as boron trifluoride-ether complex in a suitable solvent according to, for example, the method described in Tetrahedron. Lett., 36, 4759 (1989). Deacylation of the benzyl ether product thus obtained is carried out by a conventional method. That is, the deacylation can easily be carried out, for example, by reacting the benzyl ether product with a 0.01 to 1.0N methanolic solution of sodium methoxide, or the like at about −30° C. to about 50° C. for several tens minutes to several days, whereby there can be obtained the desired compound (4) wherein $R^3$ is a benzyloxy group and $R^4$ is a hydrogen atom.

By oxidizing the compound (3), there can easily be obtained an aldehyde derivative thereof having an aldehyde group at the 6-position of the non-reducing end glucose residue. A method for the oxidation is not critical so long as it permits oxidation of the hydroxyl group at the 6-position of the non-reducing end glucose residue into an aldehyde group. As such an oxidation method, oxidation with DMSO can be exemplified. It is sufficient that the oxidation is carried out by a conventional method for such a reaction with ice-cooling or upto room temperature, preferably at room temperature. The aldehyde derivative of the compound (3) can easily be obtained by reacting the compound (3) with DMSO and a carbodiimide compound such as dicyclohexylcarbodiimide in the presence of an acid catalyst such as trifluoroacetic acid or phosphoric acid in a solvent. The above ether type compound can easily be obtained also by use of the thus obtained aldehyde derivative of the compound (3). In detail, since the aldehyde group of aldehyde derivative of the compound (3) can be converted into a desired ether group according to the method described in Chem. Lett. 743 (1985), it is sufficient that the ether product thus obtained is subjected to deacylation. An explanation is given below by giving specific examples. For example, when there is produced a compound (4) wherein as in the above, $R^3$ is a benzyloxy group and $R^4$ is a hydrogen atom, the aldehyde derivative of the compound (3) is reacted with benzyl trimethylsilyl ether at a temperature of from ice-cooling to room temperature, preferably at room temperature in the presence of a catalyst such as trityl perchlorate in a solvent such as dichloromethane, after which the reaction product is reduced with triethylsilane or the like, and the resulting benzyl ether product is subjected to deacylation by a conventional method with ice-cooling or upto room temperature, preferably with ice-cooling to obtain the desired compound.

In addition, by use of the aldehyde derivative of the compound (3), there can also easily be synthesized an amine type maltooligosaccharide derivative modified in such a way that in this compound (4), $R^4$ is a hydrogen atom and $R^3$ is an amino group, a dimethylamino group, a diethylamino group, an N-ethyl-N-(β-hydroxyethyl)amino group, a benzylamino group, an anilino group, an anisidino group, a pyridylamino group or the like. In detail, the aldehyde derivative of the compound (3) is reacted with a corresponding amine such as dimethylamine, benzylamine, phenethylamine, aniline or aminopyridine to obtain a Schiff base, which is reduced with a reducing agent such as sodium cyanoborohydride, dimethylaminoborane or pyridine-borane to convert the aldehyde group into an amino group. Thereafter, other procedures such as deacylation are carried out in the same manner as in the case if the above ether type compound.

A further explanation is given below by giving a specific example. For example, when there is synthesized a compound (4) wherein $R^3$ is a pyridylamino group and $R^4$ is a hydrogen atom, 2-aminopyridine is allowed to act on the aldehyde derivative of the compound (3) to obtain a Schiff base, which is reduced into an amino compound with a reducing agent such as sodium cyanoborohydride. Then, the amino compound is subjected to deacylation by a conventional method, whereby the desired pyridylamino compound can easily be obtained.

A silyl ether type compound (4) wherein $R^4$ is a hydrogen atom and $R^3$ is a trimethylsilyl group, a dimethyl-tert-butylsilyl group, a diphenyl-tert-butylsilyl group or the like, can be obtained by reacting a corresponding silylating agent such as trimethylsilyl chloride, dimethyl tert-butylsilyl chloride or diphenyl tert-butylsilyl chloride with the compound (3) in the presence of neutralizing agent such as pyridine or triethylamine by a conventional method, followed by deacylation.

A cyclic ether type compound (4) wherein $R^3$ and $R^4$ are taken together to form a methylene ketal bridge, can be obtained by reacting a corresponding acetal compound or ketal compound with the compound (3) in the presence of an acid catalyst by a conventional method, followed by deacylation.

Of the thus obtained various maltooligosaccharide derivatives of the formula (4), most of those having an optically measurable group for $R^1$ can be used as they are as substrates for determining α-amylase activity. Those having a hydrogen atom for $R^1$ may be used as they are as substrates for determining α-amylase activity, or they may be converted into maltooligosaccharide derivatives having an optically measurable group at the reducing end, by introducing the optically measurable group by its transfer from a glycoside having the optically measurable group by use of an enzyme according to the process disclosed in Japanese Patent Unexamined Publication No. 61-83195 (U.S. Pat. No. 4,762,917). In this case, the transfer reaction using the enzyme is carried out usually under mild conditions near neutral conditions. Therefore, by this method, there can easily be synthesized without any trouble a compound (4) having a color-producing group (an optically measurable group) which cannot withstand synthesis conditions employed for modifying the 6-position of non-reducing-end glucose residue of the maltooligosaccharide derivatives.

Thus, when a compound (3) is used as an intermediate material, various maltooligosaccharide derivatives having one or more modifying groups at the 6-position or the 4- and 6-positions of the non-reducing end glucose residue can be synthesized very easily and efficiently. Also from this point of view, it is of deep significance that this invention has made it possible to obtain the compound (3) very easily in high yield.

That is, the compound (3) which can very easily be synthesized from a compound (1) by the process of this invention is a useful intermediate material for a maltooligosaccharide derivative modified at the 6-position or the 4- and 6-positions of the non-reducing end glucose residue, and therefore employment of the process of this invention has made it possible to synthesize very easily from the compound (1) various maltooligosaccharide derivatives having one or more modifying groups at the 6-position or the 4- and 6-positions of the non-reducing end glucose residue and an optically measurable group at the reducing end which are useful as substrates for determining α-amylase activity.

Examples are described below but they are not intended in any way to limit the scope of this invention.

EXAMPLE 1

Synthesis of 4-nitrophenyl O-(2,3-di-O-acetyl-α-D-glucopyranosyl)-(1→4)-O-(2,3,6-tri-O-acetyl-α-D-glucopyranosyl)-(1→4)-O-(2,3,6-tri-O-acetyl-α-D-glucopyranosyl)-(1→4)-O-(2,3,6-tri-O-acetyl-α-D-glucopyranosyl)-(1→4)-O-2,3,6-tri-O-acetyl-α-D-glucopyranoside (hereinafter abbreviated as "G5P(Ac)14")

In 50 ml of pyridine were dissolved 4.75 g of 4-nitrophenyl O-α-D-glucopyranosyl-(1→4)-O-α-D-glucopyranosyl-(1→4)-O-α-D-glucopyranosyl-(1→4)-O-α-D-glucopyranosyl-(1→4)-O-α-D-glucopyranoside (hereinafter abbreviated as "G5P") and 1.22 g of phenylboric acid, and the resulting solution was concentrated under reduced pressure at 40° to 50° C. The residue was redissolved in 50 ml of pyridine, followed by reconcentration under reduced pressure at 40° to 50° C. Then, the residue was dissolved in 50 ml of pyridine, and 30 ml of acetic anhydride was added dropwise with ice-cooling and stirring, and stirred overnight at room temperature. Thereafter, the reaction solution was poured into ice water and stirred for 3 hours. The crystals thus precipitated were collected by filtration, washed with water, and then dried under reduced pressure to obtain 6.2 g of white crystals. This product was a mixture of components different in the amount of acetyl group introduced which was composed mainly of G5P(Ac)14 (for this mixture, in the formula (3), the acyl group is an acetyl group, $R^0$ is a 4-nitrophenyl group, and n is 5; hereinafter this mixture is abbreviated as "PAG5P"). By purification from the white crystals by a column chromatography [packing: Wakogel C-200 (a trade name, Wako Pure Chemical Industries, Ltd.), eluent:1,2-dichloroethane-acetone (4:1)], 2.5 g of white crystals of G5P(Ac)14 were obtained.

IR (KBr, cm$^{-1}$): 3400, 1720, 1240, 1040.

NMR (270 MHz, CDCl$_3$): 1.9–1.1 (42H, CH$_3$), 3.4–5.8 (37H, CH, CH$_2$, OH), 7.2–7.3 (2H, arom-H), 8.2–8.3 (2H, arom-H).

EXAMPLE 2

Synthesis of G5P(Ac)14

In 100 ml of pyridine was dissolved 4.75 g of G5P, followed by adding thereto 25 g of a phenylboric acid polymer, and the resulting mixture was concentrated under reduced pressure at 40° to 50° C. To the residue was added 100 ml of pyridine, followed by reconcentration under reduced pressure at 40° to 50° C. Then, 100 ml of pyridine was added to the residue and stirred, after which the polymer was collected by filtration. In this case, 3.2 g of G5P was recovered from the mother liquor. The polymer collected by filtration was suspended in 100 ml of pyridine, and 60 ml of acetic anhydride was added dropwise with ice-cooling and stirring. After overnight standing at room temperature, the reaction solution was poured into a mixture of ice water and methylene chloride and stirred for 3 hours, and then the polymer wa filtered off. The methylene chloride layer of the mother liquor was separated, washed with water, and then dried, after which the solvent was distilled off under reduced pressure to obtain 5.9 g of PAG5P. By purification from this PAG5P by a column chromatography in the same manner as in Example 1. 1.4 g of G5P(Ac)14 was obtained.

EXAMPLE 3

Synthesis of 2-chloro-4-nitrophenyl O-(2,3-di-O-acetyl-α-D-glucopyranosyl)-(1→4)-O-(2,3,6-tri-O-acetyl-α-D-glucopyranosyl)-(1→4)-O-(2,3,6-tri-O-acetyl-α-D-glucopyranosyl)-(1→4)-O-(2,3,6-tri-O-acetyl-α-D-glucopyranosyl)-(1→4)-O-2,3,6-tri-O-acetyl-α-D-glucopyranoside (hereinafter abbreviated as "G5CNP(Ac)14")

By the same procedure as in Example 1, 2.8 g of white crystals of G5CNP(Ac)14 were obtained from 4.92 g of 2-chloro-4-nitrophenyl O-α-D-glucopyranosyl-(1→4)-α-D-glucopyranosyl-(1→4)-O-α-D-glucopyranosyl- (1→4)-O-α-D-glucopyranosyl-(1→4)-O-α-D-glucopyranoside (hereinafter abbreviated as "G5CNP").

IR (KBr, cm$^{-1}$): 3500, 1760, 1240, 1040.

NMR (270 MHz, CDCl$_3$): 1.9-2.2 (42H, CH$_3$), 3.4-5.8 (37H, CH, CH$_2$, OH), 7.3 (1H, arom-H), 8.1 (1H, arom-H), 8.3 (1H, arom-H).

EXAMPLE 4

Synthesis of
O-(2,3-di-O-acetyl-α-D-glucopyranosyl)-(1→4)-O-(2,3,6-tri-O-acetyl-α-D-glucopyranosyl)-(1→4)-O-(2,3,6-tri-O-acetyl-α-D-glucopyranosyl)-(1→4)-O-(2,3,6-tri-O-acetyl-α-D-glucopyranosyl)-(1→4)-O-(2,3,6-tri-O-acetyl-α-D-glucopyranosyl)-(1→4)-O-1,2,3,6-tetra-O-acetyl-α-D-glucopyranoside (hereinafter abbreviated as "G6(Ac)18")

By the same procedure as in Example 1, 2.7 g of white crystals were obtained from 4.8 g of O-α-D-glucopyranosyl-(1→4)-O-α-D-glucopyranosyl-(1→4)-O-α-D-glucopyranosyl-(1→4)-O-α-D-glucopyranosyl-(1→4)-O-α-D-glucopyranosyl-(1→4)-O-α-D-glucopyranose (hereinafter abbreviated as "G6").

IR (KBr, cm$^{-1}$): 3400, 1760, 1240, 1040.

NMR (270 MHz, CDCl$_3$): 1.9-2.2 (54H, CH$_3$) 3.9-5.4 (43H, CH, CH$_2$, OH) 5.7 and 6.2 (1H, H$_1$).

EXAMPLE 5

Synthesis of 4-nitrophenyl
O-(6-O-benzyl-α-D-glucopyranosyl)-(1→4)-O-α-D-glucopyranosyl-(1→4)-O-α-D-glucopyranosyl-(1→4)-O-α-D-glucopyranosyl-(1→4)-O-α-D-glucopyranoside (hereinafter abbreviated as "BG5P")

In 2 ml of methylene chloride was dissolved 770 mg of the G5P(Ac)14 obtained in Example 1, and 0.1 ml of boron trifluoride-ether complex was added. The resulting mixture was cooled to −40° C., after which 20 ml of a 0.5M solution of phenyldiazomethane in methylene chloride was added dropwise, and the resulting mixture was stirred at room temperature for 12 hours. The reaction solution was concentrated under reduced pressure, and the residue (760 mg) was dissolved in 60 ml of a 0.1N methanolic solution of sodium methoxide. The resulting solution was allowed to stand overnight at 0° to 5° C. The solvent was distilled off under reduced pressure, and the residue was dissolved in 5 ml of a 50 mM acetic acid solution. By purification from the resulting solution by use of a column of Bio-Gel P-2 (a trade name, Bio-Rad Laboratories) equilibrated with 50 mM acetic acid, 200 mg of BG5P was obtained.

HPLC: content 97% [column; packing: Wakosil, 5C18 (a trade name, Wako Pure Chemical Industries, Ltd.; 4.6×150 mm), eluents: a linear gradient between 10% CH$_3$CN-0.1% AcOH and 90% CH$_3$CN-0.1%AcOH, flow rate: 1.5 ml/min, measuring wavelength: 305 nm]. IR and NMR data of the product agreed with those of the preparation described in Japanese Patent Unexamined Publication No. 63-170393 (European Patent 252525).

EXAMPLE 6

Synthesis of BG5P

By the same procedure as in Example 5, 320 mg of BG5P was obtained using 750 mg of PAG5P obtained by the process described in Example 1.

HPLC: content 95% (the measurement conditions were the same as in Example 5).

EXAMPLE 7

Synthesis of BG5P

To a solution consisting of 308 mg of the G5P(Ac)14 obtained in Example 2, 0.16 ml of pyridine, 0.1 ml of phosphoric acid and 3 ml of DMSO was added 1240 mg of dicyclohexylcarbodiimide, and the resulting mixture was stirred at room temperature for 2 hours. The reaction solution was poured into ice water containing 200 mg of oxalic acid in solution, followed by extraction with chloroform. The chloroform layer was washed with a saturated aqueous sodium bicarbonate solution and water and then concentrated under reduced pressure. In 5 ml of methylene chloride were dissolved 153 mg of the resulting residue and 600 mg of benzyl trimethylsilyl ether, and 76 mg of trityl perchlorate was added with ice-cooling and stirred for 30 minutes. To the resulting solution was added 387 mg of triethylsilane, and the resulting mixture was stirred overnight at room temperature. The reaction solution was washed with a saturated aqueous sodium bicarbonate solution and water and then concentrated under reduced pressure to obtain 125 mg of a residue. Thereafter, deacetylation and purification were carried out by the method described in Example 5 to obtain 70 mg of BG5P.

HPLC: content 96% (the measurement conditions were the same as in Example 5).

EXAMPLE 8

Synthesis of p-nitrophenyl
O-(6-deoxy-6-(2-pyridyl)amino-α-D-glucopyranosyl)-(1→4)-O-α-D-glucopyranosyl-(1→4)-O-α-D-glucopyranosyl-(1→4)-O-α-D-glucopyranosyl-(1→4)-O-α-D-glucopyranoside (hereinafter abbreviated as "FG5P")

To a solution consisting of 308 mg of the G5P(Ac)14 obtained in Example 1, 0.16 ml of pyridine, 0.1 ml of phosphoric acid and 3 ml of DMSO was added 1240 mg of dicyclohexylcarbodiimide, and the resulting mixture was stirred at room temperature for 2 hours. The reaction solution was poured into ice water containing 200 mg of oxalic acid in solution, followed by extraction with chloroform. The chloroform layer was washed with a saturated aqueous sodium bicarbonate solution and water and then concentrated under reduced pressure. In a mixed solution of 10 ml of 6N hydrochloric acid and 10 ml of tetrahydrofuran were dissolved 155 mg of the resulting residue and 940 mg of 2-aminopyridine, and the resulting solution was stirred at room temperature for 30 minutes. Then, 1.2 g of dimethylamine borane was added, followed by stirring at room temperature for 24 hours. Water and chloroform were added to the reaction solution and stirred, after which the chloroform layer was separated, washed with a saturated aqueous sodium bicarbonate solution and water, and then concentrated under reduced pressure. The residue (140 mg) was dissolved in 100 ml of a 0.1N methanolic solution of sodium methoxide, and the resulting solution was stirred overnight with ice-cooling. The reaction solution was neutralized with acetic acid, after which the solvent was distilled off under reduced pressure, and the residue was dissolved in 5 ml of a 50 mM acetic acid solution. By purification from the resulting solution by use of a column of Bio-Gel P-2 (a trade name, Bio-Rad Laboratories) equilibrated with 50 mM acetic acid, 100 mg of FG5P was obtained.

HPLC: content 96% (the measurement conditions were the same as in Example 2).

NMR data of the product agreed with those of the preparation described in Japanese Patent Unexamined Publication No. 61-83195).

EXAMPLE 9

Synthesis of G5P(Ac)14

In 50 ml of DMF were dissolved 4.75 g of G5P and 1.22 g of phenylboric acid, and the resulting solution was concentrated under reduced pressure at 40° to 50° C. The residue was redissolved in 50 ml of DMF, followed by reconcentration under reduced pressure at 40° to 50° C. Then, the residue and 500 mg of N,N-dimethylaminopyridine (DMAP) was dissolved in 50 ml of DMF, and 30 ml of acetic anhydride was added dropwise with ice-cooling and stirring and stirred overnight at room temperature. Thereafter, the reaction solution was poured into ice water and stirred for 3 hours. The crystals thus precipitated were collected by filtration, washed with water, and then dried under reduced pressure to obtain 7.3 g of PAG5P. By purification from this PAG5P by a column chromatography in the same manner as in Example 1, 3.5 g of G5P(Ac)14 was obtained.

This invention provides a novel process for producing a polyacylmaltooligosaccharide derivative retaining the hydroxyl groups at the 4- and 6-positions of the non-reducing end glucose residue which is a useful intermediate material for producing a substrate for determining α-amylase activity which has been modified at the 6-position or the 4- and 6-positions of the non-reducing end glucose residue. The process of this invention is markedly effective in that according to said process, even when a maltooligosaccharide having a color-producing group attached thereto which is easily releasable under acidic conditions is used as a starting material, a polyacylmaltooligosaccharide derivative retaining the hydroxyl groups at the 4- and 6-positins of the non-reducing end glucose residue can be synthesized easily in high yield without any trouble. Thus, this invention contributes greatly to the synthesis and development of a substrate for determining α-amylase activity which has still higher performance characteristics.

What is claimed is:

1. A process for producing a maltooligosaccharide derivative of the formula:

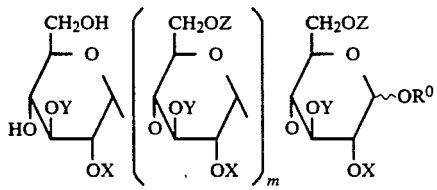

wherein $R^0$ is a hydrolyzable group, which after hydrolysis absorbs visible or ultraviolet light, or is fluorescent, or when coupled to a coupler by the action of an oxidase or by an oxidizing agent forms a dye, or is an acyl group; X, Y and Z are independently the same or different acyl groups or hydrogen, provided that X, Y and Z cannot all be hydrogen at the same time; and m is an integer of 1 to 5;

which comprises reacting an oligosaccharide compound of the formula:

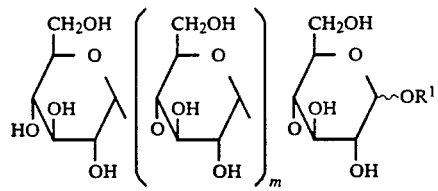

wherein $R^1$ is a hydrolyzable group as defined above or hydrogen; and m is an integer of 1 to 5, with a compound of the formula:

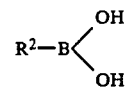

wherein $R^2$ is an alkyl, hydroxyl, alkenyl or aralkyl group, or an aryl group optionally substituted by one or more substituents selected from the group consisting of lower alkyl, lower alkoxy, nitro, amino and halogen; to convert at least the hydroxyl groups at the 4-position and the 6-position of the non-reducing end glucose residue of said oligosaccharide compound into a cyclic boric acid ester; acylating the cyclic boric acid ester; and then treating the acylated product with water.

2. A process for producing a compound of the formula:

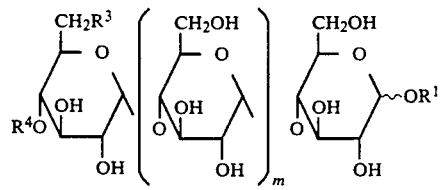

wherein $R^1$ is a hydrolyzable group, which after hydrolysis absorbs visible or ultraviolet light, or is fluorescent, or when coupled to a coupler by the action of an oxidase or by an oxidizing agent forms a dye, or is hydrogen; wherein $R^3$ is an aralkyloxy group optionally substituted by one or more substituents selected from the group consisting of lower alkyl, lower alkoxy, amino, lower-alkyl-substituted amino, carboxyl, lower alkoxycarbonyl, hydroxyl, sulfonic acid, nitro and halo; a lower alkoxy, lower alkenyloxy, or aryloxy group optionally substituted by one or more of said substituents, a pyridylmethyloxy group optionally substituted by one or more of said substituents, an amino group optionally substituted by one or more substituents selected from the group consisting of lower alkyl, lower hydroxyalkyl, aralkyl, lower-alkyl-substituted aralkyl, lower-alkoxy-substituted aralkyl, aryl, lower-alkoxy-substituted aryl, pyridyl, lower-alkyl-substituted pyridyl or lower-alkoxy-substituted pyridyl; a trialkylsilyloxy group or an alkyldiphenylsilyloxy group; $R^4$ is a hydrogen atom; $R^3$ and $R^4$ when taken together form a methylene ketal optionally substituted by one or more substituents selected from the group consisting of lower alkyl, lower alkoxy, aralkyl, and aryl groups; and m is an integer of 1 to 5;

which comprises reacting an oligosaccharide compound of the formula:

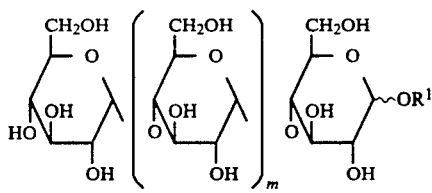

wherein $R^1$ and m are as defined above, with a compound of the formula:

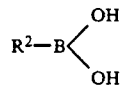

wherein $R^2$ is an alkyl, hydroxyl, alkenyl or aralkyl group, or an aryl group optionally substituted by one or more substituents selected from the group consisting of lower alkyl, lower alkoxy, nitro, amino and halogen; to convert at least the hydroxyl groups at the 4-position and the 6-position of the non-reducing end glucose residue of said oligosaccharide compound into a cyclic boric acid ester;
acylating the cyclic boric acid ester;
and then treating the acylated product with water;
replacing the hydroxyl group at the 6-position or each of the 4- and 6-positions by a modifying group other than an acyl group, and then subjecting the maltooligosaccharide derivative thus treated to deacylation.

* * * * *